US012588826B2

(12) United States Patent　(10) Patent No.: US 12,588,826 B2
Pekonen　(45) Date of Patent: Mar. 31, 2026

(54) PHOTOPLETHYSMOGRAM SENSOR ARRANGEMENT

(71) Applicant: Polar Electro Oy, Kempele (FI)

(72) Inventor: Elias Pekonen, Kempele (FI)

(73) Assignee: Polar Electro Oy, Kempele (FI)

( * ) Notice: Subject to any disclaimer, the term of this patent is extended or adjusted under 35 U.S.C. 154(b) by 590 days.

(21) Appl. No.: 17/964,200

(22) Filed: Oct. 12, 2022

(65) Prior Publication Data

US 2023/0130989 A1　Apr. 27, 2023

(30) Foreign Application Priority Data

Oct. 22, 2021　(EP) .................................... 21204132

(51) Int. Cl.
| *A61B 5/024* | (2006.01) |
| *A61B 5/026* | (2006.01) |
| *A61B 5/1455* | (2006.01) |
| *G01N 21/00* | (2006.01) |

(52) U.S. Cl.
CPC ...... *A61B 5/02427* (2013.01); *A61B 5/02438* (2013.01); *A61B 5/024* (2013.01); *A61B 5/02416* (2013.01); *A61B 5/0261* (2013.01); *A61B 5/1455* (2013.01); *A61B 5/14552* (2013.01); *G01N 21/00* (2013.01)

(58) Field of Classification Search
CPC ............ A61B 5/02427; A61B 5/02416; A61B 5/0261; A61B 5/14552; A61B 2562/185; A61B 5/02438; A61B 5/024; A61B 5/1455; A61B 2562/0233; G01N 21/00
See application file for complete search history.

(56) References Cited

U.S. PATENT DOCUMENTS

| 6,184,521 B1 * | 2/2001 | Coffin, IV .......... A61B 5/14552 |
| | | 250/237 R |
| 11,143,551 B2 * | 10/2021 | Kwangkaew ............. G01J 1/06 |
| 11,331,016 B1 * | 5/2022 | Mohammadi ...... A61B 5/14552 |
| 2002/0042558 A1 * | 4/2002 | Mendelson .......... A61B 5/1455 |
| | | 600/323 |
| 2004/0220629 A1 * | 11/2004 | Kamath ............... A61N 1/3962 |
| | | 607/6 |

(Continued)

FOREIGN PATENT DOCUMENTS

| CN | 107530000 A | 1/2018 | |
| EP | 3501380 A1 * | 6/2019 | ......... A61B 5/02416 |
| WO | 2016176218 A1 | 11/2016 | |

OTHER PUBLICATIONS

Cheng-Chun Chang et al: "MW-PPG Sensor: An on-Chip Spectrometer Approach", SENSORS, vol. 19, No. 17, Aug. 26, 2019 (Aug. 26, 2019), p. 3698, XP055657845, DOI: 10.3390/s19173698.

(Continued)

*Primary Examiner* — Sean P Dougherty
(74) *Attorney, Agent, or Firm* — FisherBroyles, LLP

(57) ABSTRACT

An apparatus includes the following: a photoplethysmogram sensor head including a light emitter and a photo detector, wherein the photo detector is disposed in a diagonal orientation with respect to a light path from the light emitter to the light detector; and an opaque mask over the photo detector, wherein the mask covers at least partially that half of the photo detector that is at a greater distance from the light emitter and leaves a remaining half of the photo detector exposed.

12 Claims, 3 Drawing Sheets

65: INNER WALL
62: WINDOW　63: WINDOW　32: MASK　66: COVER
64
31　30　60: SUBSTRATE (PCB)
31　30 32
66: COVER

(56) References Cited

U.S. PATENT DOCUMENTS

| 2012/0197093 | A1* | 8/2012 | LeBoeuf | ............. | A61B 5/7203 |
| | | | | | 250/226 |
| 2014/0276119 | A1* | 9/2014 | Venkatraman | ..... | A61B 5/02405 |
| | | | | | 600/509 |
| 2016/0213267 | A1* | 7/2016 | Laakkonen | .......... | A61B 5/6826 |
| 2016/0310027 | A1* | 10/2016 | Han | ................... | A61B 5/02427 |
| 2017/0209055 | A1* | 7/2017 | Pantelopoulos | ..... | A61B 5/7203 |
| 2023/0380692 | A1* | 11/2023 | Huttunen | ............... | G06F 1/163 |

OTHER PUBLICATIONS

Nogami Hirofumi et al: "Relationship between AC/DC Ratio and Light-blocking Structure for Reflective Photoplethysmographic Sensor", Sensors and Materials., [Online] vol. 30, No. 12, Dec. 28, 2018 (Dec. 28, 2018), pp. 3021-3028, XP055909138, JP ISSN: 0914-4935, DOI: 10.18494/SAM.2018.1989 Retrieved from the Internet: URL:https://sensors.myu-group.co.jp/sm_pdf/SM1738.pdf> [retrieved on Apr. 4, 2022].
Extended European Search Report received for EP Patent Application Serial No. 21204132.1 dated Apr. 13, 2022, 10 pages.
Office Action issued in corresponding Chinese Application Serial No. 202211289981.7, dated Jul. 3, 2025, 9 pages.

* cited by examiner

PHOTOPLETHYSMOGRAM SENSOR ARRANGEMENT

CROSS-REFERENCE TO RELATED APPLICATION

This application claims benefit and priority to European Application No. 21204132.1, filed Oct. 22, 2021, which is incorporated by reference herein in its entirety.

BACKGROUND

Technical Field

The present invention relates to a field of optical biometric measurements and, in particular, to measuring a photoplethysmogram of a user.

SUMMARY

A cardiogram may be measured by various sensors. A photoplethysmogram (PPG) sensor is an example of a cardiogram sensor. A PPG sensor conventionally comprises at least one light source, such as a light emitting diode (LED), and at least one photo sensor such as a photodiode. Light emitted by the LED(s) is directed to a skin of a user wearing the PPG sensor, and the light is delivered via the skin to the photodiode(s). An electrocardiogram (ECG) sensor is another type of heart activity sensor that is configured to measure electrical heart activity by using one or more electrodes attached to the user's skin.

Physical dimensions of the light source and the photo sensor form a rectangle. A conventional arrangement of the rectangular photo sensor with respect to the light source is illustrated in FIG. 1. The light source (light emitter 10) and the photo sensor (photo detector 12) are arranged such that a side of the photo sensor closest to the light source is substantially perpendicular to the direction of a line (dotted line in FIG. 1) from the light source to the photo sensor. In other words, when looking from the light source, the photo sensor is seen as a rectangle. It has been observed that this arrangement is sub-optimal for the PPG measurements. This is illustrated in the curves above the photo detector 12.

The curves illustrate the intensity of the light received from the light emitter at the various parts along the photo detector in the particular arrangement of FIG. 1 and, further, a ratio between a pulsatile component (AC) and a non-pulsatile component (DC) of a PPG measurement signal. The AC/DC ratio is important in the detection of the heart activity because the greater AC/DC ratio means the greater AC component and the greater amplitude of the PPG measurement signal, allowing better detection of the PPG signal peaks. The light intensity is important in the sense that it reflects the portion of the light propagated from the light emitter 10 with respect to noise. Greater intensity means greater signal-to-noise ratio. As illustrated in FIG. 1, the particular arrangement of the photo detector 12 with respect to the light emitter results in a solution where the light intensity is greatest at the portion of the photo detector 12 where the AC/DC component is at its minimum. In general, the curves are inversely proportional with respect to the spatial distribution of the photo detector. In any particular spot on the photo detector, either the intensity or the AC/DC component is small.

The invention is defined by the independent claim. Various embodiments are provided in the dependent claims.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figures 1, 2:
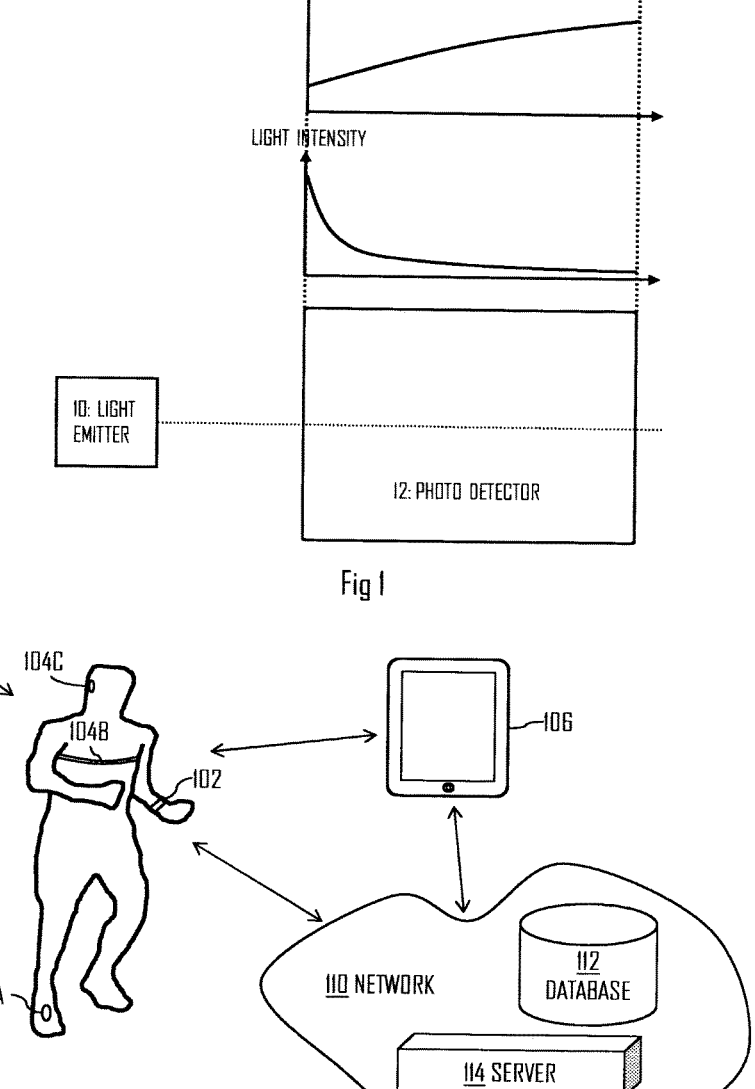
FIG. 1 illustrates a conventional arrangement of a photoplethysmogram sensor head.
FIG. 2 illustrates a system to which embodiments of the invention may be applied.

FIG. 2 illustrates a system to which embodiments of the invention may be applied. Said system may be used to monitor physical training, activity, and/or inactivity of a user 100. Thus, the embodiments may not be limited to monitoring and/or measuring physical training of the user 100, and thus said system may be used to monitor physical activity and/or inactivity during the day and/or night (e.g. 24 hours a day). Such may be possible by using one or more devices described with respect to FIG. 1 and in the embodiments below.

Referring to FIG. 1, the user 100 may wear a wearable device, such as a wrist device 102, a head sensor unit 104C, a torso sensor 104B, and/or a leg sensor 104A. In another example, the wearable device may be and/or be comprised in glasses. In another example, the wearable device is comprised or configured to be coupled with a garment or garments (or apparel). Examples of such garments may include bra(s), swimming apparel, such as swimming suit or cap, and glove(s). The garment or apparel may be worn by the user. In some embodiments, the wearable device is integrated as a part of the garment or apparel. Due to simplicity reasons, let us now describe the wearable device as being the wrist device 102. However, embodiments described in relation to wrist device 102 may be utilized by other types of wearable devices, i.e. the embodiments are not necessarily limited to wrist device or devices 102.

The wrist device 102 may be, for example, a smart watch, a smart device, sports watch, and/or an activity tracking apparatus (e.g. bracelet, arm band, wrist band, mobile phone). The wrist device 102 may be used to monitor physical activity of the user 100 by using data from internal sensor(s) comprised in the wrist device 102 data from external sensor device(s) 104A-C, and/or data from external services (e.g. training database 112). It may be possible to receive physical-activity-related information from a network 110, as the network may comprise, for example, physical activity-related information of the user 100 and/or some other user(s). Thus, the wrist device 102 may be used to monitor physical activity related information of the user 100 and/or the other user(s). Naturally, one or more of the external sensor device(s) 104A-C may be worn by the other user(s), and thus information received from said one or more sensor device(s) 104A-C may be monitored from the wrist device 102 by the user 100. The network 110 may comprise the training database 112 and/or the server 114. The server 114 may be configured to enable data transfer between the training database 112 and some external device, such as the wearable device. Hence, the database 112 may be used to store cardiac activity measurement data, for example.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol, for example. Other wireless communication methods, such as Wireless Local Area Network (WLAN) and/or Near Field Communication (NFC), may also be used.

The wrist device 102 may comprise a heart activity sensor configured to determine cardiac activity of the user 100, such as heart rate, heart beat interval (HBI) and/or heart rate variability (HRV), for example. The heart activity sensor may comprise an optical cardiac activity sensor unit configured to measure the cardiac activity of the user 100 by using optical measurements. An example of such sensor is a PPG (photoplethysmography) sensor. A sensor head of a PPG sensor may comprise one or more light emitting diodes (LEDs) as light emitter(s) and a photo detector such as a photodiode. The optical measurements may comprise the LED(s) emitting light towards a body tissue of the user 100 and measuring the bounced, reflected, diffracted, scattered and/or emitted light from the body tissue of the user 100 by using the photodiode. The emitted light is modulated when travelling through veins of the user 100 and the modulation may be detected by the optical cardiac activity sensor unit. By using detected optical measurement data, the wrist device 102 may determine cardiac activity of the user 100, such as the heart rate. The optical cardiac activity sensor unit may obtain via the measurement a measurement signal characterizing or carrying the cardiac activity information on the user. As understood, similar cardiac activity circuitry may be comprised in the other wearable devices described herein.

It also needs to be noted that the cardiac activity circuitry may produce raw measurement data of the cardiac activity and/or it may process the measurement data into cardiac activity information, such as heart rate for example. The sensor(s) in the cardiac activity circuitry may comprise data processing capabilities. Also, the wrist device 102 and/or some other wearable device may comprise a processing circuitry configured to obtain the cardiac activity measurement data from the cardiac activity circuitry and to process said data into cardiac activity information, such as a cardiac activity metric characterizing the cardiac activity of the user 100. For example, the measurement data of the optical cardiac activity sensor unit may be used, by the processing circuitry, to determine heart rate, HRV and/or HBI of the user 100. Further, the raw measurement data and/or processed information may be processed by the wrist device 102 or some other wearable device, and/or transmitted to an external device, such as the portable electronic device 106.

The wrist device 102 (or more broadly, the wearable device) may comprise other types of sensor(s). Such sensor(s) may include a Laser Doppler-based blood flow sensor, a magnetic blood flow sensor, an Electromechanical Film (EMFi) pulse sensor, a temperature sensor, a pressure sensor, an electrocardiogram (ECG) sensor, and/or a polarization blood flow sensor.

The wearable device comprising the PPG sensor head may comprise a casing and a fixing mechanism configured to attach said casing to an object such as the user 100. The fixing mechanism may be a wrist strap in a case where the portable training computer is the wrist computer. The fixing mechanism may be the apparel to which the portable training computer may be integrated or removably attached. The casing may house at least some of the electronic circuits of the portable training computer. The casing may further store a power source of the portable training computer, e.g. a battery.

A communication circuitry may provide the wearable device with capability of transmitting and receiving signals and data wirelessly. The communication circuitry may comprise a radio modem configured to operate according to one or more radio communication protocols such as Bluetooth® technology developed within Bluetooth Special Interest Group (SIG). The supported Bluetooth technology may include Bluetooth Smart®, Bluetooth Low energy (BTLE) or, in general, any one or more of the Bluetooth evolution versions from version 1.0 up to 5.0 and beyond in the future. In another embodiment, the radio modem supports another communication technology such as a global navigation satellite system (GNSS) technology such as the Global Positioning System or Galileo. In another embodiment, the radio modem supports ultra-wideband (UWB) technology. In an embodiment, the portable training computer comprises multiple radio modems supporting different radio communication protocols and operating on different frequency bands. The communication circuitry may be used to transmit the data acquired from the PPG measurement signals to any one of the devices 102, 106, 114, depending on the particular embodiment.

Figure 3:
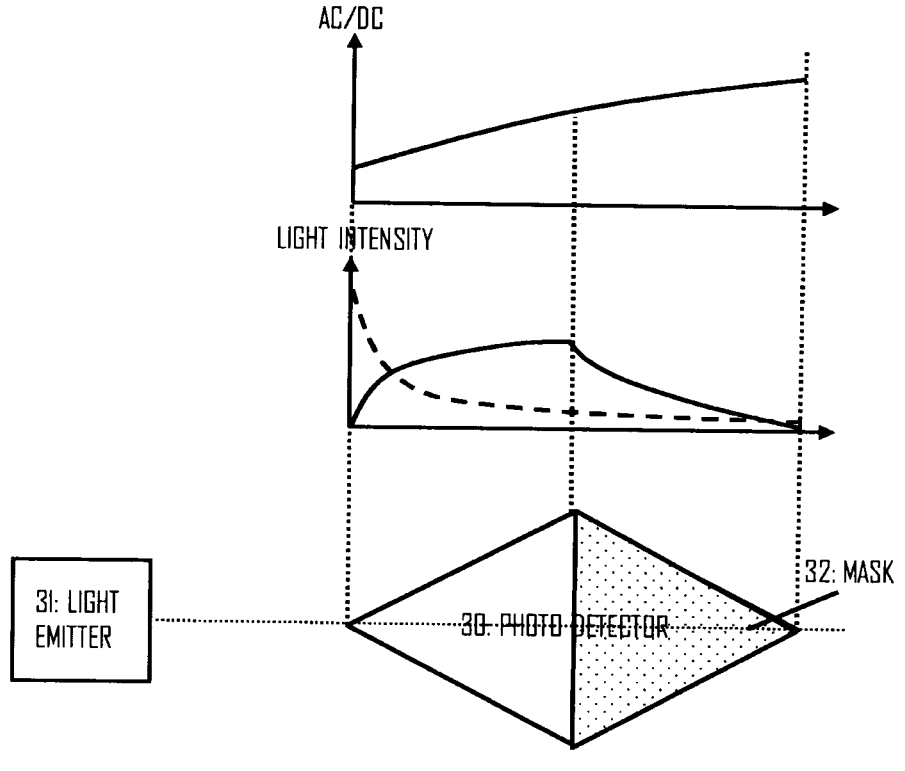
FIG. 3 illustrates an arrangement of a photoplethysmogram sensor head according to an embodiment.

FIG. 3 illustrates a PPG sensor head for any one of the above-described apparatuses comprising the PPG sensor. Referring to FIG. 3, the PPG sensor head comprises a light emitter 31 that may be similar to the light emitter 10 and a photo detector 30. The light emitter may comprise a light emitting diode. The photo detector 30 is disposed into a diagonal orientation with respect to a light path from the light emitter to the light detector. Rotating the photo detector about 45 degrees with respect to the arrangement of FIG. 1 provides a different curve for the light intensity. The AC/DC curve remains substantially similar to that of the arrangement of FIG. 1. The light intensity curve of the arrangement of FIG. 1 is drawn to the light intensity diagram of FIG. 3 (dashed line) for comparison. As can be seen, the light intensity curve of the diagonal photo detector has a maximum at the mid-point of the photo detector where the photo detector is widest along the path from the light emitter 31 to the photo detector (dotted horizontal line in FIG. 3). The light intensity drops about exponentially after the mid-point. Now, the light intensity is high at the sections of the photo detector where the AC/DC component is also high or at least greater than in the arrangement of FIG. 1. It means that the light components collected by the respective areas of the photo detector have high signal-to-noise ratio and high AC/DC, thus increasing PPG measurement signal amplitude with respect to the arrangement of FIG. 1.

Since the light intensity decreases quite rapidly at the half of the photo detector that is farther away from the light emitter, light components collected by the farther half have a lower signal-to-noise ratio although the AC/DC is at its highest. Because of this characteristic, it is beneficial to mask at least some parts of the farther half of the photo detector surface in order to improve the total signal-to-noise ratio of the PPG measurement signal. For the purpose of masking, an opaque mask 32 is disposed over the photo detector 30. The mask 32 covers at least partially that half of the photo detector that is at a greater distance from the light emitter 31, leaving the other half of the photo detector exposed to collect the light from the light emitter.

Needless to say, the light emitter and the photo detector are arranged on the same plane or substrate, and the above-described distance is measured on that plane. In the context of the PPG sensors, both the light emitter and the photo detector are arranged on the same plane and directed to the same general direction, towards the skin. The light emitter emits the light to that direction while the photo detector collects the light from that direction.

The mask may cover a majority of the farther half of the photo detector, e.g. including the corner farthest from the light emitter. The mask may cover only the farthest of the corners of the photo detector, or it may cover three of the four corners and the farther half of the photo detector, leaving the corner closest to the light emitter exposed to the light.

The shape of the photo detector may be a square or a rectangle that has been rotated into the diagonal orientation from the viewpoint of the light emitter. The definition of the square or rectangle also applies to squares or rectangles having sharp corners as well as squares or rectangles having rounded corners. Alternatively, the shape of the photodetector can be a parallelogram or a rhombus or another geometric shape having four or at least four corners.

The mask 32 may be realized with any physical component or coating on the photo detector that would realize the opaque characteristic and prevent the light from reaching the covered part of the photo detector 30. Accordingly, the light components with low signal-to-noise ratio are excluded from the PPG measurement signal measured by the photo detector, thus improving the signal-to-noise ratio of the PPG measurement signal and increasing the amplitude of the PPG measurement signal.

Let us then describe the meaning of the diagonal orientation. The apparatus of claim 1, wherein the photo detector is aligned such that a diagonal of the photo detector is codirectional with the light path. The diagonal in FIG. 3 is the diagonal drawn by the horizontal dotted line through the photo detector. It should be understood that some deviation may be allowed without changing the light intensity profile substantially. Accordingly, the diagonal may deviate from the direction of the light path by 10 degrees or less, for example. The rotation obviously changes the light intensity profile towards that of FIG. 1, thus bringing the peak of the light intensity to a zone where the AC/DC component is lower.

From another perspective, the diagonal orientation may be understood such that, when looking from the direction of the light emitter 31, the photo diode is observed as rather having a diagonal (diamond) form than a rectangular (square) form. It means that a rotation of at least 20 degrees from the orientation of FIG. 1 would push the light intensity peak to a zone where the AC/DC component is higher, thus providing some benefits to the amplitude of the PPG measurement signal.

Yet from another perspective, the diagonal orientation may be understood such that a point (a corner) instead of a side of the photo detector 30 is the part of the photo detector that has the shortest distance to the light emitter 31.

It should be understood that the light emitter 31 and the photo detector 30 form a PPG sensor configured together to measure the PPG measurement signal. The light emitter is needed to emit light to the user's 10 skin and the photo detector is needed to collect the light emitted travelled from the light emitter via the skin. Obviously, the light is collected by the exposed part of the photo detector.

Figure 4:
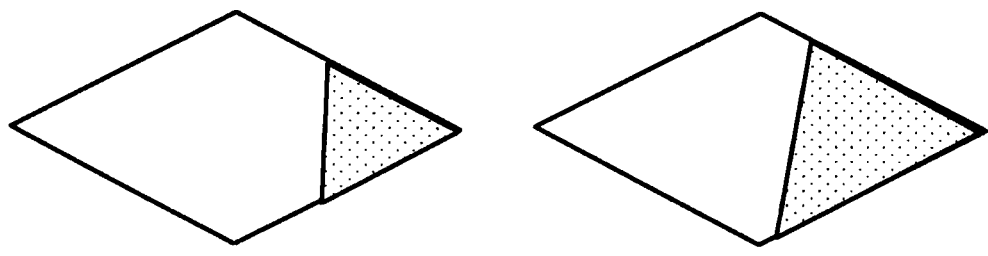
FIG. 4 illustrates some embodiments of masking a photo detector.

Let us then disclose some embodiments of how the mask covers at least partially the more distant half of the photo detector, when viewed from the light emitter. The more distant half may be defined as a continuous or uniform area of the photo detector starting from a point of the photo detector 30 furthest to the light emitter 31 and extending towards the light emitter 31. FIG. 4 illustrates some embodiments where less than half of the photo detector is covered by the mask, but the covered part covers a certain amount of the area furthest away from the light emitter. The mask may be symmetric or asymmetric with respect to the shape of the photo detector, as illustrated in FIG. 4.

In the embodiment of FIG. 3, the mask 32 fully covers the half of the photo detector that is at said greater distance from the light emitter. In case the photo detector is not symmetric from the viewpoint of the light emitter, e.g. the photo detector is rotated more than zero degrees but less than 45 degrees with respect to the photo detector of FIG. 1, the mask may cover the half that forms a continuous or uniform area starting from the furthest point of the photo detector with respect to the light emitter and extends from there towards the photo emitter.

Figure 5:
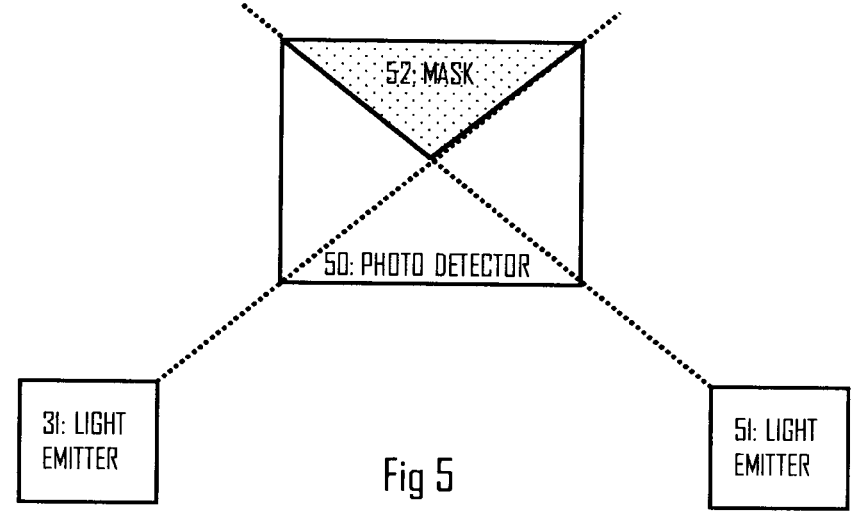
FIG. 5 illustrates an arrangement of a photoplethysmogram sensor head according to another embodiment.

In an embodiment, the apparatus comprises a further light emitter, and the photo detector is disposed into a diagonal orientation with respect to a light path from the further light emitter to the photo detector. FIG. 5 illustrates such an embodiment where light emitters 31, 51 are disposed such that the photo detector 50 (may be identical to the photo detector 30) is diagonal with respect to both light emitters 31, 51. In other words, different corners of the photo detector may point to the different light emitters 31, 51, 7. The light emitters 31, 51 may be disposed on the same side of the photo detector but at different angles from the perspective of the photo detector. The light emitters may be disposed into the same general direction from the photo detector, thus leaving at least a part of the photo detector that is the furthest with respect to both light emitters 31, 51.

Similar to the embodiment of FIG. 3, the mask 52 may in this embodiment cover at least partially that half of the photo detector that is at a greater distance from the further light emitter and leaves the other half of the photo detector exposed. FIG. 5 illustrates an embodiment of the area covered by such a mask. In the arrangement of FIG. 5, direct lines from the light emitter 31 and the further light emitter 51 are drawn through the photo detector. The lines with the intersection of the lines divide a photo detection area of the photo detector into quadrants. The mask covers at least partially that quadrant of the photo detector that is at the greatest distance from both the light emitter 31 and the further light emitter 51.

In general, the exposed part of the photo detector may form a triangle or a combined area of multiple triangles (excluding a rectangle as the combined area) where each light emitter faces a corner of at least one of the triangle(s). In the embodiment of FIG. 3, the triangle is easily visible. In the embodiment of FIG. 5, the exposed area is formed by two triangles according to the same logic as in FIG. 3.

Figure 6:
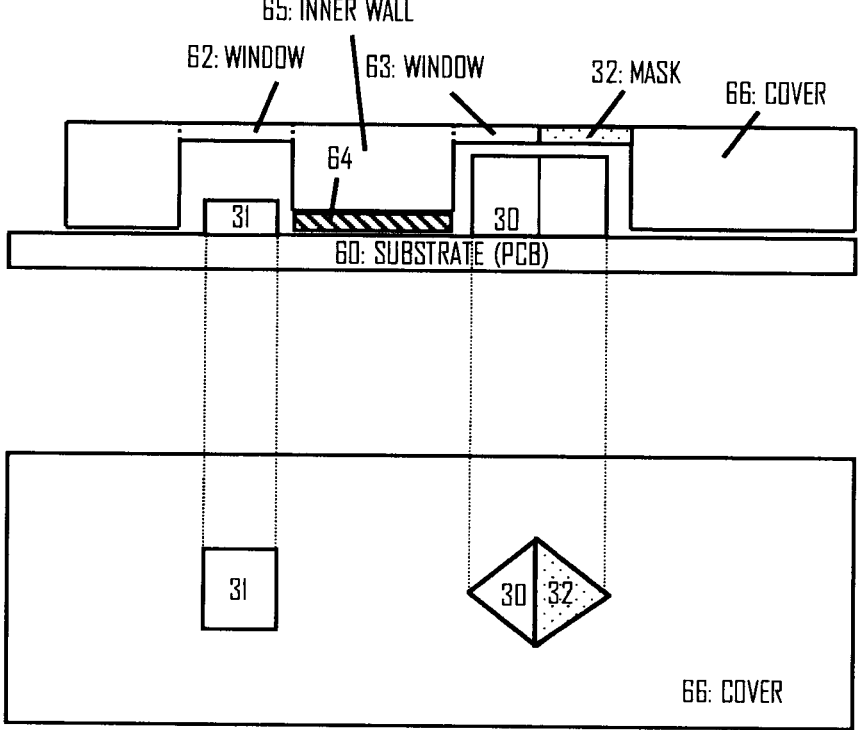
FIG. 6 illustrates an arrangement of a housing for a photoplethysmogram sensor head according to any embodiment described herein.

In an embodiment, the apparatus described in connection with any one of the embodiments above comprises a circuit board housing the light emitter(s) 31, 51 and the photo detector 30. FIG. 6 illustrates such an embodiment where the circuit board is more generally presented by a substrate 60. The circuit board may be a rigid of flexible printed circuit board. The apparatus may further comprise a cover 66 disposed on the circuit board. The cover comprises a first window 62 at a location of the light emitter and a second window 63 at a location of the photo detector 30. In the embodiments having multiple light emitters, respective windows may be provided. The windows may be holes etched to the cover or made of transparent material filling or covering the holes. The cover may be plastics of metal, for example, and further comprise a transparent layer that covers the windows 62, 63 to prevent the holes from clogging. In the embodiment of FIG. 6, the mask 32 is arranged in the cover and in connection with the second window. The mask may be an integral part of a body of the cover and of the same material as the cover 66. The mask may thus be realized so that the second window 63 is etched so that it exposes only the half (part) of the photo detector that is closer to the light emitter(s) and designed to be exposed according to the embodiments described above. Therefore, implementation of the mask 32 needs no additional components or layers but it can be formed by the cover. However, other embodiments may realize the mask as a separate component arranged in connection with the second window 63 in the cover 66.

FIG. 6 illustrates the apparatus as a side view and as a top view, thereby illustrating also the diagonal shape and orientation of the photo detector 30 with respect to the light emitter 31.

In an embodiment, the cover has at least one opaque protrusion 65 extending towards the circuit board between the light emitter 31 and the photo detector 30, thus blocking direct propagation of light from the light emitter to the photo detector inside the apparatus. In other words, an outer surface of the cover (designed to face the skin) may define a surface or a plane, and the protrusion extends from this plane towards the substrate and, in an embodiment, extends to contact with the substrate, either directly or via a gasket or a seal 64. As described above, the purpose of the inner wall is to prevent light noise at the photo detector. The protrusion may extend at least to the level where it blocks direct line-of-sight from the light emitter to the photo detector at least for the most part of the surfaces of the light emitter to the photo detector that face one another. In other words, the surface of the light emitter facing the photo detector has no direct line-of-sight to the majority of the surface of the photo detector that faces the light emitter. In an embodiment, there is no direct line-of-sight between the two surfaces. This reduces the light noise compared to conventional solutions where the inner wall protrudes from the substrate towards the cover, or is provided as an additional component, leaving a small gap between the inner wall and the cover and/or the substrate. The light from the light emitter may reach the photo detector from such a gap, causing the light noise. The inner wall may be an integral part of the cover, e.g. made of the same uniform material as the other parts of the cover.

It will be obvious to a person skilled in the art that, as the technology advances, the inventive concept can be implemented in various ways. The invention and its embodiments are not limited to the examples described above but may vary within the scope of the claims.

The invention claimed is:

1. An apparatus comprising:

a photoplethysmogram sensor head comprising a light emitter and a photo detector arranged on a same plane, wherein a photo detection area of the photo detector has a shape having at least four corners and wherein the photo detector is disposed in a diagonal orientation with respect to a light path from the light emitter to the photo detector such that a closest point of the photo detector with respect to the light emitter is one of the corners of the photo detection area of the photo detector; and an opaque mask over the photo detector, the mask covering at least partially a half of the photo detection area of the photo detector that is at a greater distance from the light emitter, thereby preventing light from the light emitter from reaching the covered part of the photo detector and leaving the remaining half of the photo detector exposed to collect the light from the light emitter.

2. The apparatus of claim 1, wherein the photo detector is aligned such that a diagonal of the photo detector is codirectional with the light path.

3. The apparatus of claim 1, wherein the mask covers a continuous area of the photo detection area of the photo detector starting from a point of the photo detector furthest from the light emitter and extending towards the light emitter.

4. The apparatus of claim 3, wherein the mask fully covers the half of the photo detection area of the photo detector that is at said greater distance from the light emitter.

5. The apparatus of claim 1, further comprising a further light emitter, wherein the photo detection area of the photo detector is disposed in a diagonal orientation with respect to a light path from the further light emitter to the photo detector.

6. The apparatus of claim 5, wherein the mask covers at least partially the half of the photo detection area of the photo detector that is at a greater distance from the further light emitter and leaves the remaining half of the photo detection area of the photo detector exposed.

7. The apparatus of claim 5, wherein the light emitter and the further light emitter are disposed on a same side but at different angles from the perspective of the photo detector.

8. The apparatus of claim 5, wherein an intersection of direct lines from the light emitter and the further light emitter through the photo detector divide the photo detection area of the photo detector into quadrants, and wherein the mask covers at least partially a quadrant of the photo detector that is at the greatest distance from both the light emitter and the further light emitter.

9. The apparatus of claim 1, wherein the light emitter is configured to emit light to a skin of a user when the apparatus is attached to the user, and the photo detector is configured to collect, with at least the exposed half, the light emitted by the light emitter and travelled via the skin and to generate a photoplethysmogram measurement signal based on the collected light.

10. The apparatus of claim 1, wherein the apparatus is a wearable training computer.

11. The apparatus of claim 1, further comprising:

a circuit board housing the light emitter and the photo detector; and a cover disposed on the circuit board, wherein the cover comprises a first window at a location of the light emitter and a second window at a location of the photo detector, wherein the mask is arranged in the cover and in connection with the second window.

12. The apparatus of claim 11, wherein the cover has at least one opaque protrusion extending towards the circuit board between the light emitter and the photo detector, thereby blocking direct propagation of light from the light emitter to the photo detector inside the apparatus.

\* \* \* \* \*